United States Patent [19]

Marinus et al.

[11] Patent Number: 5,048,534
[45] Date of Patent: Sep. 17, 1991

[54] METHOD OF AND DEVICE FOR DETERMINING QUANTITIES CHARACTERIZING THE FLOW OF A LIQUID IN A VASCULAR SYSTEM

[75] Inventors: Johannes L. M. Marinus; Paulus A. C. Van Dongen, both of Eindhoven, Netherlands

[73] Assignee: U.S. Philips Corporation, New York, N.Y.

[21] Appl. No.: 388,285

[22] Filed: Aug. 1, 1989

[30] Foreign Application Priority Data

Aug. 9, 1988 [NL] Netherlands .................. 8801982

[51] Int. Cl.$^5$ .................................. A61B 5/0275
[52] U.S. Cl. ................................ 128/691; 128/654; 128/713
[58] Field of Search .................. 128/654, 691, 713; 358/111; 378/99

[56] References Cited

U.S. PATENT DOCUMENTS

| | | | |
|---|---|---|---|
| 4,006,736 | 2/1977 | Kranys et al. ................ 128/2 A |
| 4,456,926 | 6/1984 | Kruger et al. . | |
| 4,536,790 | 8/1985 | Kruger et al. . | |
| 4,692,864 | 9/1987 | Shimani et al. ............... 378/99 X |
| 4,716,904 | 1/1988 | Meno ............................. 128/713 X |

OTHER PUBLICATIONS

O. Nalcioglu et al., "Quantitative Aspects of Image Intensifier-Television-Based Digital X-ray Imaging," Digital Radiography, Chapter 5, J. G. Kereiakes, S. R. Thomas & C. G. Orton (Eds), Plenum Publishing Corp., 1986.
Technical Notes, vol. 23, No. 7, Mar. 1972, S. M. Larson et al.: "Radioisotope Technique for Measuring Regional Organ Blood Flow", pp. 388-390.
Medical Physics, vol. 8, No. 5, Sep./Oct. 1981, "Estimation of the Diameter of and Iodine Concentration Within Blood Vessels Using Digital Radiography-Devices", pp. 652-658.
Biomedizinische Technik, vol. 23, No. 9, 1978, pp. 208-215, R. Sonne et al.: "Vergleihende Untersuchungen Verschiedener Messmethoden Sur Blutflussbestimmung-Aus Digitalen Angiogrammen".
Radiology, vol. 161, No. 2, Nov. 1986, pp. 323-328, D. K. Swanson et al, "Arterial Blood-flow Waveform Measurement in Intact Animals" New Digital Radiographic Technique.

*Primary Examiner*—Richard J. Apley
*Assistant Examiner*—L. Thomas
*Attorney, Agent, or Firm*—William Squire

[57] ABSTRACT

A part of the vascular system which may be considered to consist of an entrance vessel (33), a reservoir (37) and an exit vessel (35) is arranged in an apparatus for making subtraction images by means of penetrating radiation, a contrast medium which absorbs radiation being introduced into the entrance vessel. During the flowing of the liquid mixed with contrast medium from the entrance vessel (33), via the reservoir (37), to the exit vessel (35), a series of subtraction images is made. For successive subtraction images having the ranks n and n+1 in the series a part (43) of the entrance vessel (33) which adjoins the reservoir and a part (45) of the exit vessel (35) which adjoins the reservoir are determined for which the equation $$\Delta TD_{res}(n) = TD_{in}(n) - TD_{ex}(n+1)$$

is satisfied, where $TD_g(n)$ generically refers to the right hand expressions and is defined as the total radiographic density of a region g in the subtraction image having the rank n, and where $\Delta TD_{res}(n)$ is defined as $$\Delta TD_{res}(n) = TD_{res}(n+1) - TD_{res}(n)$$

and where the subscripts res, in and ex refer to the reservoir, part of the entrance vessel, and part of the exit vessel, respectively.

4 Claims, 1 Drawing Sheet

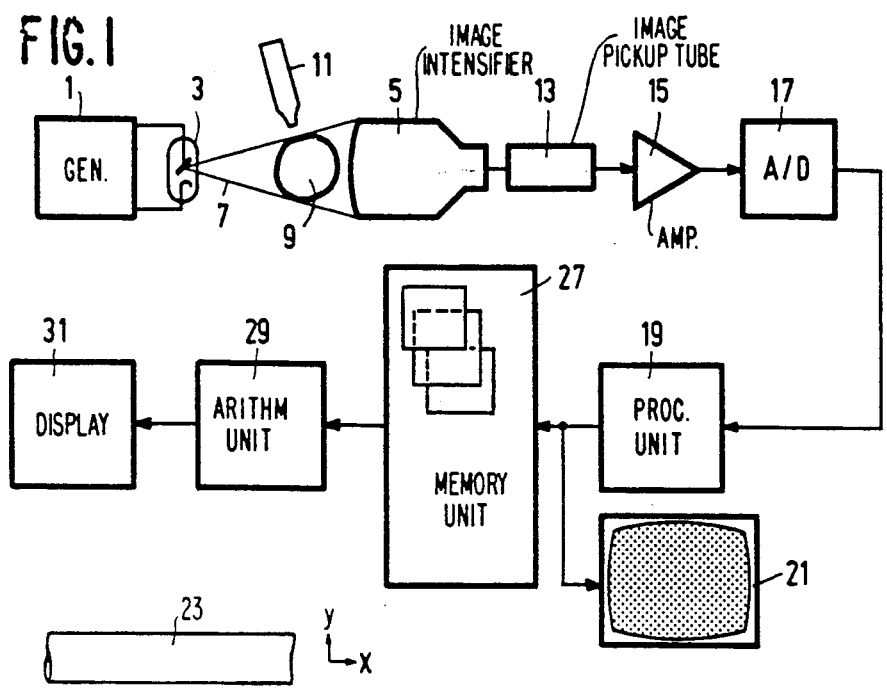
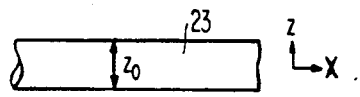
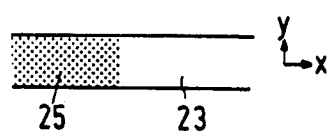
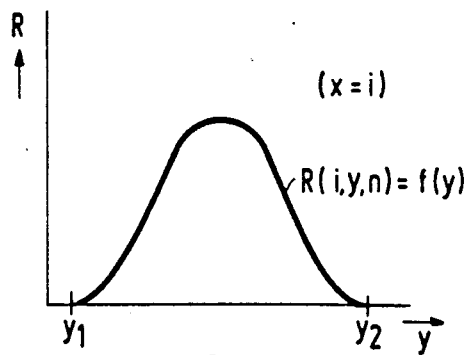
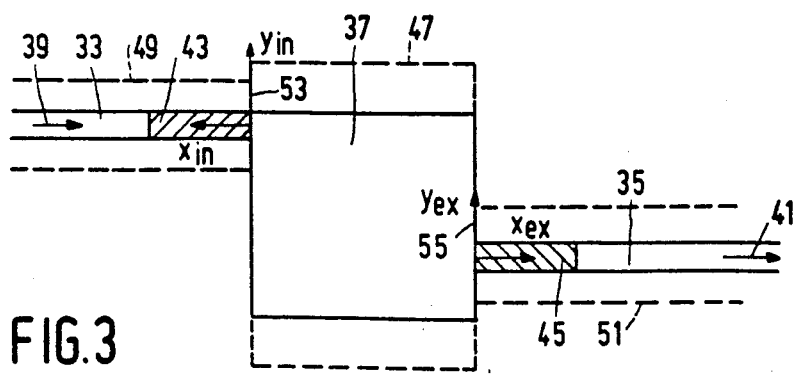

METHOD OF AND DEVICE FOR DETERMINING QUANTITIES CHARACTERIZING THE FLOW OF A LIQUID IN A VASCULAR SYSTEM

BACKGROUND OF THE INVENTION

1. Field of the Invention

The invention relates to a method of determining quantities characterizing the flow of a liquid in a part of a vascular system, which part may be considered to comsist of an entrance vessel, a reservoir and an exit vessel, the method comprising the steps of arranging part of the vascular system in an apparatus for making subtraction images by means of penetrating radiation, introducing a radiation-absorbing contrast medium into the entrance vessel, making a series of subtraction images while the liquid mixed with the contrast medium flows from the entrance vessel, via the reservoir, to the exit vessel, and deriving the quantities characterizing the flow from the differences in radiographic density TD of successive subtraction images, which are due to the displacement of the contrast medium. The invention also relates to a device for determining quantities characterizing the flow of a liquid in a part of a vascular system, which part may be considered to consist of an entrance vessel, a reservoir and an exit vessel, which device comprises dosing means for introducing contrast medium into the entrance vessel and an apparatus for making a series of subtraction images which represent the displacement of the contrast medium in said part of the vascular system.

2. Description of the Prior Art

A method and a device for making subtraction images by means of penetrating radiation (in this case X-rays) are described, for example in EP-A-0 096 941. The radiation passes through an object to be examined and is converted into a visible image by means of an X-ray image intensifier, i.e. the so-called X-ray image. This image represents the transmitted X-rays. According to the subtraction technique used, a "contrast-filled" X-ray image is subtracted from a contrast-free X-ray image. Before the subtraction is carried out, the logarithm of both X-ray images is taken. Thus, a logarithmic differential image or subtraction image is obtained. The density of each pixel in the subtraction image is proportional to the amount of contrast medium present in an elementary volume of the irradiated object which is projected onto the pixel (in both X-ray images). From the density in principle a variety of other values (for example, the local contrast concentration and the local irradiated thickness of the vessel) can be calculated. This density is referred to as the radiographic density.

A method of the kind set forth is known from Radiology 161 (1986), pp. 323-328. In accordance with the known method, the reservoir is formed by a central part of a blood vessel, a proximal part of which constitutes the entrance vessel and a distal part of which constitutes the exit vessel. When two successive subtraction images having the rank n and n+1 in the series are considered, the total radiographic density in the central part of the blood vessel can be measured in the first image n, and in the second image n+1 a part of the central part which adjoins the distal part can be searched in which the total radiographic density is equal to the value measured in the image n. The length thereof is smaller than the length of the central part and the difference is the distance travelled by the liquid (the blood) during the period of time $\Delta t$ elapsing between the making of the two X-ray images n and n+1 wherefrom the subtraction images n and n+1 have been formed. When the contrast medium has already progressed as far as the distal part in the first image n, a correction must be made for the amount of contrast material, or radiographic density, which has flowed from the central part into the distal part during the period $\Delta t$. The publication discloses how this correction can be determined.

The known method is of limited use only, because the reservoir must consist of a part of a single, non-branched blood vessel. The measurement of the flow from and to an organ in which the reservoir is formed by branching blood vessels which communicate on the one side with a single entrance vessel and on the other side with a single exit vessel, is not possible. A second drawback of the known method consists in that it can be used only if the concentration of the contrast material in the reservoir exhibits a gradient.

SUMMARY OF THE INVENTION

It is an object of the invention to provide method which takes into account the spatial variation as well as the variation in time of the radiographic density and which does not impose special requirements as regards the course or the nature of the vessels in the reservoir or as regards the distribution of the contrast material in the reservoir.

To achieve this, the method in accordance with the invention is characterized in that for successive subtraction images having the ranks n and n+1 in the series a part of the entrance vessel which adjoins the reservoir and a part of the exit vessel which adjoins the reservoir are determined for which the following equation is satisfied:

$$\Delta TD_{res}(n) = TD_{in}(n) - TD_{ex}(n+1)$$

where $TD_g(n)$ is defined as the total radiographic density of a region g in the subtraction image having the rank n, where $\Delta TD_{res}(n)$ is defined as $$\Delta TD_{res}(n) = TD_{res}(n+1) - TD_{res}(n)$$

and where the subscripts res, in and ex refer to the reservoir, part of the entrance vessel, and part of the exit vessel, respectively.

The method in accordance with the invention utilizes the location-dependent variation (TD) as well as the time-dependent variation ($\Delta TD$) of the radiographic density (amount of contrast material). Because the variation of the total radiographic density in the reservoir $\Delta TD_{res}$ is determined, it is not important how the radiographic density and hence the contrast material is distributed in the reservoir. As a result, the course of the vessels in the reservoir does not have an effect, not even when it changes between the formation of two X-ray images, for example due to motions in the body containing the vascular system examined.

The device in accordance with the invention comprises a memory unit for storing the radiographic density of the pixels of at least two successive subtraction images of the series, and an arithmetic unit which is suitable for determining, for successive subtraction images having the ranks n and n+1 in the series, a part of the entrance vessel which adjoins the reservoir and a part of the exit vessel which adjoins the reservoir, for which parts the following equation is satisfied $$\Delta TD_{res}(n) = TD_{in} - TD_{ex}(n+1)$$

where $TD_g(n)$ is defined as the total radiographic density of a region g in the subtraction image having the rank n, where $\Delta TD_{res}(n)$ is defined as $$\Delta TD_{res}(n) = TD_{res}(n+1) - TD_{res}(n)$$

and where the subscripts res, in and ex refer to the reservoir, part of the entrance vessel, and part of the exit vessel, respectively.

IN THE DRAWING

The invention will be described in detail hereinafter with reference to the drawing. Therein:

FIG. 1 shows a block diagram of an embodiment of a device in accordance with the invention, FIGS. 2a-2e show a number of images of a blood vessel in order to illustrate the method of forming images by means of the device shown in FIG. 1, FIG. 3 diagrammatically shows a part of a vascular system, and FIG. 4 shows a graph illustrating an alternative version of the method in accordance with the invention.

DESCRIPTION OF THE PREFERRED EMBODIMENT

The device which is diagrammatically shown in FIG. 1 comprises an X-ray tube 3 which is powered by a high-voltage generator 1 and which separates an X-ray beam 7 which is directed onto an X-ray image intensifier 5. An object 9 to be examined, for example a person or an animal, is located in the beam. Using a known injector 11 (see, for example U.S. Pat. No. 4,006,736), an amount of X-ray-absorbing contrast medium is injected at a suitable point in a vascular system present in the object 9.

The X-ray beam 7 irradiates the object 9, after which the transmitted radiation is incident on the X-ray image intensifier 5 which produces a visible image of the structures present in the object (see, for example U.S. Pat. No. 4,536,790). This image will be referred to hereinafter as an X-ray image. Using an image pick-up tube 13, the X-ray image is converted into a video signal which is converted, after amplification in an amplifier 15, into a digital signal by means of an analog-to-digital converter 17. The video level in each pixel of the X-ray image is determined by the amount of radiation transmitted by an elementary volume of the object which is projected onto this pixel. Subsequently, the digital signal is processed in a processing unit 19 in order to form logarithmic differential images where an X-ray image of the object made before injection of the contrast medium is subtracted from an X-ray image made after injection of the contrast medium after the logarithm of both X-ray images has been taken. These logarithmic differential images (referred to hereinafter as subtraction images) represent substantially exclusively the vessels filled with the contrast medium, without the disturbing effect of other structures in the object 9, because this effect was present to the same degree in both X-ray images and has disappeared after subtraction.

The subtraction images and the original X-ray images may be displayed, for example on a display screen of a first display unit 21. The device described thus far is known; for example, see EP-A-0 096 941 for further details. The subtraction technique described thus far is also known; for example, see U.S. Pat. No. 4,456,926.

Using the described device, before, during and after the injection of contrast medium X-ray images can be made in rapid succession, which images visualize the progression of the contrast medium in the vascular system or a part thereof. Similarly, a succession of subtraction images can be formed in which the progression of the contrast material is visualized without the disturbing effect of other structures in the object. Each of the subtraction images comprises a number of pixels whose density depends on the amount of contrast material locally present in a vessel (provided that no other structures filled with contrast medium are projected onto the same pixel) as will be described with reference to FIG. 2.

FIGS. 2a and 2b are two representations of the anatomy of a blood vessel 23 and FIG. 2c shows an X-ray image of the same vessel as can be displayed on the display screen of the display unit 21. At in FIG. 2a, a projection of the blood vessel 23 is shown in the x-y plane of a rectangular coordinate system whose X-axis coincides with the axis of the blood vessel. At in FIG. 2b a projection in the x-z plane is shown. When the X-ray beam 7 (see FIG. 1) extends according to the z-axis, after the injection of the contrast medium an X-ray projection in the x-y plane of the vessel 23 partly filled with contrast medium is obtained on the display screen of the display unit 21 as indicated at in FIG. 2c. In this X-ray image the shaded region denoted by the reference numeral 25 is visible, in which contrast medium is present. Subsequently, a subtraction image is formed by taking the logarithmic difference between the contrast-free X-ray image and the contrast-filled X-ray image. On the basis of the Lambert-Beer law, the density in each pixel of the subtraction image thus formed is linearly proportional to the amount of contrast medium locally present in the vessel at the instant of detection of the contrast-filled X-ray image. This density is referred to hereinafter as the radiographic density and is used notably in densitometric image analysis techniques. Numerous examples of densitometric analysis methods are described in the literature. The method disclosed hereinafter is based on the radiographic density determined in each pixel of the subtraction image, that is to say, in a rapid succession so that the progression of the contrast medium can be studied.

The literature describes a number of phenomena which could disturb the linear relationship between the radiographic density and the local amount of contrast medium; however, for these phenomena corrections are possible in order to restore the linear relationship. A number of disturbances and the associated corrections are described, for example in chapter 5 of Digital Radiography, J. G. Kereiakes, S. R. Thomas and C. G. Orton (Eds.), Plenum Publishing Corporation 1986.

In principle two methods are known for the measurement of the flow of the liquid in a vessel, based on the assumption that the flow of the contrast medium is representative of the flow of the carrying liquid. On the one hand use can be made of time-dependent information (the variation of the radiographic density, i.e. also the concentration of the contrast medium if the irradiated thickness of the vessel is constant, at a given location as a function of time); on the other hand, use can be made of location-dependent information (location-dependent variations of the radiographic density at predetermined instants). Numerous examples of both methods are described in the literature. The cited publication Radiology 161, pp. 323-328 describes an example of the second method.

For optimum use of the information supplied by the processing unit 19, however, it is desirable to combine the two methods in a suitable manner. To this end, the device which is diagrammatically shown in FIG. 1 also comprises a memory unit 27 for storing the radiographic density of the pixels of at least two successive X-ray images (subtraction images) processed by the processing unit 19, and also comprises an arithmetic unit 29 for performing a number of calculations which are described in detail hereinafter. The result of these calculations are reproduced a second display unit 31 which may be combined, if desired, with the first display unit 21 so as to form one unit. It will be apparent that it is alternatively possible to apply the information obtained by means of the device to another device (not shown) for further processing or storage. It will also be evident that the memory unit 27 need not be permanently connected to the processing unit 19. Once when the information supplied by the processing unit 19 has been stored in the memory unit 27 either directly or via an additional record carrier (not shown), the memory unit can operate independently together with the arithmetic unit 29 and possibly the second display unit 31, the other part of the device being available again for a next measurement.

The following considerations serve to illustrate the calculations to be performed by the arithmetic unit 29.

A vascular system (for example, the vascular system of a person or an animal) consists of a network of vessels in which a liquid (for example blood) flows. The contrast medium injected into this vascular system by the injector 11 is mixed with this liquid and is distributed through the vascular system. In some regions it is possible to consider a part of the vascular system in which an entrance vessel and an exit vessel with an intermediate region which is referred to as a reservoir can be distinguished. In the reservoir the vessels may be branched in a random manner; however, it may also be a central part of a single vessel in which a proximal part forms the entrance vessel and a distal part forms the exit vessel. The entrance vessel and/or the exit vessel may alternatively consist of two or more vessels which extend approximately in the same direction and which form a comparatively simple structure so that together they can be considered to form a single vessel. When the amount of contrast medium in the reservoir is determined at two different instants, the difference between these two amounts must be equal to the difference between the amount having flowed into the reservoir via the entrance vessel during the period elapsing between these two instants and the amount having flowed out of the reservoir via the exit vessel during the same period. The invention utilizes the recognition of this fact for determining quantities which are characteristic of the flow in such a part of a vascular system.

FIG. 3 diagrammatically shows a part of a vascular system which satisfies the above conditions. The entrance vessel is denoted by the reference numeral 33, the exit vessel is denoted by the reference numeral 35 and the reservoir is denoted by the reference numeral 37. The liquid flows from left to right as denoted by arrows 39 and 41. The contrast medium is injected into the entrance vessel 33, or in a location upstream therefrom, after which a series of X-ray images or subtraction images is made by means of the device shown in FIG. 1; during this operation the liquid mixed with the contrast medium flows from the entrance vessel, via the reservoir 37, to the exit vessel 35. These images are stored in the memory unit 27. During the period of time elapsing between the formation of two successive X-ray images having the ranks n and n+1 in the series, a quantity of liquid flows from the entrance vessel 33 into the reservoir 37. This quantity consists of a liquid column 43 which is situated in the part of the entrance vessel 33 which adjoins the reservoir 37 when the image n is formed. At the same time an equal quantity of liquid flows from the reservoir 37 into the exit vessel 35. This quantity forms a liquid column 45 which is present in the part of the exit vessel 35 which adjoins the reservoir 37 when the image n+1 is made. The variation of the quantity of contrast medium in the reservoir 37 must be equal to the difference between the quantities of contrast medium flowing in and out. It will be evident that the same holds good for the radiographic density which is proportional to the quantity of contrast medium.

In the logarithmic subtraction images as supplied by the processing unit 19 of FIG. 1 the radiographic density R in each pixel is proportional to the local quantity of contrast medium. The total radiographic density measured in a given region of interest g, in the image n is defined as:

$$TD_g(n) = \sum_g R(x, y, n) \tag{1}$$

Therein, R(x, y, n) is the local radiographic density of the pixel having the coordinates (x, y) in the subtraction image n and summing takes place over all pixels in the region g.

When the total radiographic density in the reservoir 37 is determined in two subtraction images n and n+1, the difference between these two values must be equal to the difference between the in-flowing and the out-flowing radiographic density, i.e.

$$\Delta TD_{res}(n) = TD_{in}(n) - TD_{ex}(n+1) \tag{2}$$

Therein, the subscripts res, in and ex refer to the reservoir 37, the part of the entrance vessel 33 which adjoins the reservoir and contains the in-flowing liquid column 43, and the part of the exit vessel 35 which adjoins the reservoir and contains the out-flowing liquid column 45. Furthermore, the following definition holds for $\Delta TD_{res}(n)$:

$$\Delta TD_{res}(n) = TD_{res}(n+1) - TD_{res}(n) \tag{3}$$

The reservoir 37 has fixed dimensions and $TD_{res}$ can be simply determined by summing the local radiographic densities R in a region 47, which is denoted by broken lines and which is slightly larger than the reservoir. The axial dimensions of the parts of the entrance vessel 33 and the exit vessel 55 to be taken into account are not predetermined and must be determined so that the equation (2) is satisfied. In order to ensure that each of the two vessels is taken into account over its full width, the radiographic densities can be taken into account in regions which laterally extend along the vessels and adjoin the reservoir 37. These regions are denoted by broken lines in FIG. 3, the region associated with the entrance vessel 33 being denoted by the reference numeral 49 whilst the region associated with the exit vessel 35 is denoted by the reference numeral 51. The arithmetic unit 29 can determine the total radiographic densiy in increasingly larger parts of the regions 49 and 51 which adjoin the reservoir 37 until the values for $TD_{in}(n)$ and $TD_{ex}(n+1)$ have been found for which the equation (3) is satisfied. According to this method, therefore, the spatial distribution of the radiographic density (in the liquid columns 43 and 45) as well as the variation in time of the local distribution (in the reservoir 37) is taken into account.

For the determination of $TD_{in}(n)$ and $TD_{ex}(n+1)$, for example the following method can be used.

First of all, for the entrance vessel 33 as well as for the exit vessel 35 a coordinate system is selected with an x-axis and an y-axis and an origin which is situated at the location where the relevant vessel changes over into the reservoir; the x-axis is coincident with the axis of the relevant vessel (thus it may be curved if the vessel exhibits one or more bends) and is directed away from the reservoir 37, whilst the y-axis extends perpendicular to the axis of the vessel and parallel to the plane of the subtraction image. In FIG. 3 these coordinate systems are denoted by the reference numerals 53 for the entrance vessel 33 and 55 for the exit vessel 35. When the radiographic density R is plotted as a function of y at a given distance from the reservoir 37 for which x=i, a local density curve R(i, y, n)=f(y) as shown in FIG. 4 is obtained. In this Figure the boundaries of the region 49 or 51 considered are denoted by the references $y_1$ and $y_2$. Outside the vessel the radiographic density is equated to zero and it increases gradually from the walls of the vessel in the direction of the axis. For different values of i the arithmetic unit 29 determines the area ATDP below the local density curve RC(i, y, n):

$$ATDP(i,n) = \sum_{y=y_1}^{y=y_2} R(i, y, n) \quad (4)$$

Therefore, this is the total radiographic density in a disc-shaped region at the area x=i which extends perpendicular to the y axis. For a part of the vessel having a length v adjacent the reservoir 37, the total radiographic density TD enclosed by this part is determined from:

$$TD(v,n) = \sum_{i=o}^{i=v} ATDP(i,n) \quad (5)$$

For every two images n and n+1 in which the total density in the reservoir $TD_{res}$ is different, $TD_{in}(v_{in}, n)$ and $TD_{ex}(v_{ex}, n+1)$ are determined in the described manner. By step-wise incrementing $v_{in}$ and $v_{ex}$, ultimately given values for $v_{in}$ and $v_{ex}$ are found for which the equation (2) is satisfied. Because the amounts of liquid flowing into and out of the reservoir per unit of time are the same, $v_{in}$ and $v_{ex}$ must always be chosen so that the volumes of the entrance vessel and the exit vessel which are taken into account are equal. If the diameters of the two vessels are equal, $v_{in}$ is, therefore, equal to $v_{ex}$. If the diameters are not equal, a correction must be included in each iteration step in order to make the volumes added in each step the same. This means that each step-wise increase of the upper limit of the summing operation in the equation (5) must be weighted with the local volume of the relevant vessel. As a result, it may even be that an individual ATDP contributes only partly to the sum of the equation (5). The resultant values for $v_{in}$ and $v_{ex}$ will be different, but the volumes of the liquid columns 43 and 45 will be the same.

The above correction can be used if relative estimates of the local volumes of the vessels are available. This volume can be approximated by the product of the surface of the local cross-section of the vessel and the axial dimension of a pixel. The local cross-section itself can be approximated when the local diameter of the vessel is known. These local diameters can be estimated, for example by means of the local ATDPs found in the image if the vessel is uniformly filled with contrast medium. A suitable method in this respect is described in Medical Physics, 8 No. 5 (1981), pp. 652–658.

By dividing the values $v_{in}$ and $v_{ex}$ found by the time $\Delta t$ elapsing between the making of the images n and n+1, the mean flow rates in the vessels 33 and 35 are found. By dividing the estimated volume of one of the liquid columns 43 and 45 by $\Delta t$, the volume flow is found. The described method can be used for any pair of successive subtraction images for which the density in the reservoir 37 is different. Therefore, the method is based on the treatment of individual subtraction image pairs of the already processed X-ray images. By treating the entire series in this manner, the flow rate or the volume flow as a function of time is found.

It is alternatively possible to use a second method which is based on the fiction that at any instant the contrast material is uniformly distributed over a given length of the vessel (the entrance vessel 33 and/or the exit vessel 35). This fictitious constant quantity per volume unit can be calculated from the mean value of the actual quantity in a predetermined volume V of the vessel having a length d. The total radiographic density TD(d, n) in this volume in accordance with the equation (5) equals:

$$TD(d,n) = \sum_{i=o}^{i=d} ATDP(i,n)$$

The mean density per volume unit MTD(n) then amounts to:

$$MTD(n) = \frac{TD(d,n)}{V(d)} = \frac{1}{V(d)} \sum_{i=o}^{i=d} ATDP(i,n) \quad (6)$$

When the length $d_{in}$ and $d_{ex}$ of the entrance vessel 33 and the exit vessel 35, respectively, taken into account are chosen so that $V_{in} = V_{ex}$ and when subsequently $MTD_{in}(n)$ and $MTD_{ex}(n+1)$ are calculated by means of (6), the equation (2) becomes:

$$\Delta TD_{res}(n) = f(n) \{ MTD_{in}(n) - MTD_{ex}(n+1) \} \quad (7)$$

Therein, f(n) is a multiplication factor having the dimension "volume" which is necessary for satisfying the law of maintaining the amount of contrast medium (or radiographic density). Therefore, in order to satisfy the equation (2), f(n) must be chosen so that the equation (7) is satisfied. The value of f(n) divided by $\Delta t$ (the period of time elapsing between the two exposures) directly produces the volume flow Q(n), for example in ml/s. When this volume flow is divided by the area of the local cross-section of the vessel (which can be estimated in the manner described with reference to the first method), the local flow rate c(n) is found.

When the value of Q(n) and/or c(n) associated with each image pair is thus determined for all image pairs of a series of subtraction images, a suitable approximation of the variation of the volume flow and/or the flow rate as a function of the time Q(t) or c(t), respectively, is obtained.

In order to determine the volume flow Q(t) or the flow rate c(t) in accordance with the second method, therefore the arithmetic unit 29 must be suitable for performing the described calculations. These are elementary calculations which can be executed, for example by means of a suitably programmed microprocessor.

In the foregoing, versions of the method in accordance with the invention have been described in which the flow of blood in a vascular system was studied. It will be evident that the method can be used equally well for studying the flow in any other vascular system, for example, a network of ducts, provided that in this system a part can be found which can be considered to consist of only a single entrance vessel, a reservoir and a single exit vessel.

In addition to the use of X-rays, other penetrating radiation which is absorbed by a suitable contrast medium, for example ultrasonic waves, can also be used for making subtraction images.

What is claimed is:

1. A method of determining quantities characterizing the flow of a liquid in a part of a vascular system, which part comprises an entrance vessel (in), a reservoir (res) and an exit vessel (ex), the method comprising the steps of arranging said part of the vascular system in an apparatus for making subtraction images by means of penetrating radiation, introducing a radiation-absorbing contrast medium into the entrance vessel, making a series of subtraction images while the liquid mixed with the contrast medium flows from the entrance vessel, via the reservoir, to the exit vessel, and deriving the quantities characterizing the flow from the difference in radiographic density TD of successive subtraction images which are due to the displacement of the contrast medium, for successive subtraction images having the ranks n and n+1 in the series, a part of the entrance vessel which adjoins the reservoir and a part of the exit vessel which adjoins the reservoir are determined for which the following equation is satisfied:

$$\Delta TD_{res}(n) = TD_{in}(n) - TD_{ex}(n+1) \quad (2)$$

where $TD_g(n)$ generically refers to each of the right hand expressions and is defined as the total radiographic density of a region g in the subtration image having the rank n, where $\Delta TD_{res}(n)$ is defined as $$\Delta TD_{res}(n) = TD_{res}(n+1) - TD_{res}(n) \quad (3)$$

and where the subscripts res, in and ex refer to the reservoir, part of the entrance vessel, and part of the exit vessel, respectively.

2. A method as claimed in claim 1 wherein the determination of $TD_{in}$ and $TD_{ex}$ comprises the following steps:
   (a) selecting a coordinate system having an x-axis and a y-axis, whose origin is situated at the location where the relevant vessel changes over into the reservoir, and whose x-axis coincides with the axis of the relevant vessel and is directed away from the reservoir, the y-axis extending perpendicular to the axis of the vessel and parallel to the plane of the subtraction image;
   (b) determining of the local radiographic density R (x, y) of each pixel (x, y) in a selected region which adjoins the reservoir and wherethrough the relevant vessel extends;
   (c) determining for different values x=i the area ATDP below the local density curve R=f (y), which area for the $n^{th}$ subtraction image equals:

$$ATDP(i, n) = \sum_{y=y_1}^{y=y_2} R(i, y, n) \quad (4)$$

where $y_1$ and $y_2$ are situated outside the boundaries of the relevant vessel;
   (d) determining, for a part of the vessel having a length the total radiographic density TD enclosed by this part from the equation:

$$TD(v, n) = \sum_{i=0}^{i=v} ATDP(i, n) \quad (5)$$

(e) step-wise incrementing the upper limit v of the summing operation performed in step (d) for the entrance vessel as well as for the exit vessel until the values of the entrance vessel length $v_{in}$ and exit vessel length $v_{ex}$ for which the equation (2) is satisfied are reached.

3. A method as claimed in Claim 1 wherein the determination of the parts of the entrance vessel and the exit vessel for which the equation (2) is satisfied comprises the following steps:
   (a) selecting a coordinate system having an x-axis and a y-axis, whose origin is situated at the location where the relevant vessel changes over into the reservoir, and whose x-axis coincides with the axis of the relevant vessel and is directed away from the reservoir, the y-axis extending perpendicular to the axis of the vessel and parallel to the plane of the subtraction image;
   (b) determining the local radiographic density R (x, y) of each pixel in a selected region, which adjoins the reservoir and wherethrough the relevant vessel extends;
   (c) determining for different values x=i the area ATDP below the local density curve R=f (y), which area for the $n^{th}$ subtraction image is defined as:

$$ATDP(i, n) = \sum_{y=y_1}^{y=y_2} R(i, y, n) \quad (4)$$

where $y_1$ and $y_2$ are situated outside the boundaries of the relevant vessel;
   (d) selecting a part of the entrance vessel which adjoins the reservoir and has a length $d_{in}$ and a volume $V_{in}$ and a part of the exit vessel which adjoins the reservoir and has a length $d_{ex}$ and a volume $V_{ex}$, so that $V_{in} = V_{ex}$;
   (e) determining for the selected parts of the entrance vessel and the exit vessel the mean radiographic density per volume unit $MTD_{in}(n)$ and $MTD_{ex}(n+1)$, respectively, from the equation:

$$MTD(n) = \frac{1}{V} \sum_{i=0}^{i=d} ATDP(i, n)$$

Where V is volume and $= V_{in} = V_{ex}$ and $d = d_{in}$ and $d = d_{ex}$, respectively;

(f) determining from the mean radiographic density per volume unit of the entrance vessel $MTD_{in}(n)$ and the exit vessel $MTD_{ex}(n+1)$ and from $\Delta TD_{res}(n)$ a factor $f(n)$ for which the equation $$\Delta TD_{res}(n) = f(n)\{MTD_{in}(n) - Mtd_{ex}(n+1)\} \qquad (7)$$

is satisfied.

4. A device for determining quantities characterizing of the flow of a liquid in a part of a vascular system, which part comprises an entrance vessel, a reservoir, and an exit vessel, which device comprises: dosing means for introducing contrast medium into the entrance vessel; means for generating a series of subtraction images which represent the displacement of the contrast medium in said part of the vascular system; memory means for storing the radiographic of the pixels of at least two successive subtraction images of the series; and arithmetic means responsive to the stored pixel densities for determining, for successive subtraction images having the ranks n and n+1 in the series, a part of the entrance vessel (in) which adjoins the reservoir (res) and a part of the exit vessel (ex) which adjoins the reservoir for which parts the following equation is satisfied:

$$\Delta TD_{res}(n) = TD_{in}(n) - TD_{ex}(n+1) \qquad (2)$$

where $TD_g(n)$ generically refers to each of the right hand expressions and is defined as the total radiographic density of a region g in the subtraction image having the rank n, where $\Delta TD_{res}(n)$ is defined as $$\Delta TD_{res}(n) = TD_{res}(n+1) - TD_{res}(n) \qquad (3)$$

and where the subscripts res, in and ex refer to the reservoir, part of the entrance vessel, and part of the exit vessel, respectively.

* * * * *